(12) United States Patent
Xu et al.

(10) Patent No.: US 10,266,880 B2
(45) Date of Patent: Apr. 23, 2019

(54) METHOD FOR QUANTITATIVE MEASURING SHORT RNA USING AMPLIFIED DNA FRAGMENT LENGTH POLYMORPHISM

(71) Applicant: Chengdu Nuoen Biological Technology Co., Ltd., Chengdu (CN)

(72) Inventors: Kai Xu, Missouri, TX (US); Fang Tang, Chengdu (CN); Yaoyi Zhang, Chengdu (CN); Zihao Feng, Chengdu (CN); Yu Yang, Chengdu (CN); Xiujin Wu, Chengdu (CN); Feifei Zhang, Chengdu (CN)

( * ) Notice: Subject to any disclaimer, the term of this patent is extended or adjusted under 35 U.S.C. 154(b) by 100 days.

(21) Appl. No.: 15/500,027

(22) PCT Filed: Sep. 15, 2015

(86) PCT No.: PCT/CN2015/089566
§ 371 (c)(1),
(2) Date: Jan. 28, 2017

(87) PCT Pub. No.: WO2016/015686
PCT Pub. Date: Feb. 4, 2016

(65) Prior Publication Data
US 2019/0017108 A1    Jan. 17, 2019

(30) Foreign Application Priority Data

Jul. 28, 2014 (CN) .......................... 2014 1 0362696

(51) Int. Cl.
| | | |
|---|---|---|
| *C12Q 1/68* | (2018.01) | |
| *C12Q 1/6851* | (2018.01) | |
| *C12P 19/34* | (2006.01) | |
| *C12Q 1/6869* | (2018.01) | |
| *C12Q 1/6855* | (2018.01) | |

(52) U.S. Cl.
CPC ............ *C12Q 1/6851* (2013.01); *C12P 19/34* (2013.01); *C12Q 1/6855* (2013.01); *C12Q 1/6869* (2013.01); *C12Q 2535/138* (2013.01); *C12Q 2545/114* (2013.01); *C12Q 2600/16* (2013.01)

(58) Field of Classification Search
None
See application file for complete search history.

(56) References Cited

U.S. PATENT DOCUMENTS

2011/0033858 A1*  2/2011  Futami ................. C12Q 1/6851
435/6.16

* cited by examiner

*Primary Examiner* — Stephanie K Mummert
(74) *Attorney, Agent, or Firm* — Novoclaims Patent Services LLC; Mei Lin Wong

(57) ABSTRACT

The present invention relates to the technical field of molecular biology, provides a method for measuring short RNA using amplified DNA fragment length polymorphism, and comprises the following steps: first using at least two synthesized miRNAs as the internal measurement standard, said synthesized miRNAs containing no natural homologous sequence in comparison with the short RNA to be measured, and mixing the synthesized miRNAs using different molecule numbers so as to form a dynamic miRNA standard molecular gradient; mixing the same quantity of the dynamic miRNA standard with the short RNA to be measured, and performing RNA reverse transcription, cDNA tailing, PCR synchronous amplification, and fluorescent quantitative analysis on the length polymorphism fragment of the PCR product DNA so as to measure the relative ratio of the fluorescence intensity of the DNA fragment produced by the amplification of the short RNA to be measured to the dynamic miRNA standard fluorescence intensity gradient.

15 Claims, 7 Drawing Sheets
Specification includes a Sequence Listing.

METHOD FOR QUANTITATIVE MEASURING SHORT RNA USING AMPLIFIED DNA FRAGMENT LENGTH POLYMORPHISM

CROSS REFERENCE OF RELATED APPLICATION

This is a national phase national application of an international patent application number PCT/CN2015/089566 with a filing date of Sep. 15, 2015, which claimed priority of Chinese application number 201410362696.2, filing date Jul. 28, 2014. The contents of these specifications, including any intervening amendments thereto, are incorporated herein by reference.

BACKGROUND OF THE PRESENT INVENTION

Field of Invention

The present invention relates to the field of molecular biotechnology, and more particularly to a method for quantitatively measurement of short-chain RNAs using amplified fragment length polymorphism of DNA.

Description of Related Arts

MicroRNA (miRNA) belongs to a class of short-chain and single-stranded RNAs which regulates gene expression and consists of about 22 nucleotides (nt). MiRNA is involved in different types of cell activities, which influence and participate in the maintenance of physiological and differentiation status of cells, a particular change in the miRNA expression level can also reflect the physiological and pathological characteristics of organisms, which suggests its potential as a biomarker for the identification of a plurality of diseases. For example, miR-122 is unique in liver cells and changes in quantity of miR-122 in blood can reveal the damage condition of liver. miR-122 is unique to liver cells and each human liver cell has 130,000 number of miR-122, and that the mir-122 has the specificity and sensitivity which is not found in biomarkers currently used for liver injury identification. Although the role of miRNA in this pathological changes remains to be clarified and the mechanism needs to be further studied, this has become one important direction of research in miRNA in which the objectivity, sensitivity and standardization of quantitative detection methods of miRNA are the bottleneck factors and keys to move the miRNA research results to applications in clinical diagnosis.

It is known that humans have more than 1,000 types of miRNAs, and the dynamic range of the expression quantity of miRNA which is related to different specific physiological and pathological phenomena is very great, which range from single digit level to tens of thousands. In addition, miRNAs process characteristics of very short length, similar sequence, secondary structure, terminal modification and length difference, which lead to a very great challenge to purification and precision quantification of miRNA.

At present, the current major applications used for miRNA quantification analysis include PCR quantitative reverse transcription (RT-qPCR), miRNA sequencing (miR-seq) which has the ability of simultaneous detection of multiple miRNAs, microArray hybridization assays. There are also many other high-throughput technology platforms based on RNA/DNA hybridization technology such as NanoString nCounter and nanopore technology. However, due to the imperfections of these methods themselves, which are lack of sensitivity and accuracy, it may take some time for their realization and actual application.

The major problem in the practical application of the miRNA testing method is sensitivity. For example, the NanoString nCounter method has the highest sensitivity and has a lower limit of 1 amol, that is about $6 \times 10^5$ number of molecules or more, whereas miR-seq and microArray has a lower limit of 0.1 fmol, that is $6 \times 10^7$ $6 \times 10^5$ number of molecules or more. Apparently these do not meet the needs of most molecular diagnostics.

Wherein the miR-seq method does not depend on the miRNA sequence on miRNA identification and has an irreplaceable effect for discovery of new species of miRNA. Also, a relative readings of miRNA can be statistically calculated and there are many studies using it for exploration of a lot of pathological diagnosis applications, which discover a lot of beneficial signs. However, the miR-seq sample processing requires the use of RNA Ligase and DNA ligase to prepare suitable cDNA library, relative quantification can be detected on the machine only after PCR amplification. Lengthy sample preparation process and the use of a variety of modified enzymes will destroy the linear correlation of the target for testing and the readings obtained and affect the objectivity of the miRNA determination. Therefore, absence a better preparation method, miR-seq cannot be used for miRNA quantitative measurement.

RT-qPCR is the most sensitive, objective and reliable method for the detection of RNA in modern molecular biology diagnostic method. The method is fast and does not require any special equipment. Traditionally, RT-qPCR is targeted for long-chain RNA such as mRNA, the primer length is usually 20 nt or above. However, the total length of mature miRNA is about 22 nt and the detection of miRNA by RT-qPCR requires special modification process to make it suitable for qPCR. In addition to stem-loop primers which can be used for miRNA RT, locked nucleotide primers (LNA) and poly (A) polymerase plus tail-oligo(dT) triggered RT is also applied to miRNA quantitative measurement. The real-time fluorescent PCR assay represented by reverse transcription-qPCR method with the TaqMan probe and the stem-loop primer has the ability to assay single-copy miRNA molecules and is widely used in miRNA mechanism research, disease diagnosis, treatment prognosis and other researches. This is because it is the most sensitive, objective and easily applied method among all existing methods, and is the most preferred method for validating miRNA expression profiles obtained by microArray and miR-seq methods. Despite the continuous technological improvements and the strengthening of the process continue to spawn new miRNA qPCR detection method, there are at least two major barriers which deter the acceptance of these technologies in clinical applications, which are quality assessment of the method and standardization of the method. These two obstacles seriously affect the reproducibility of results obtained from the method in different batches, operators and laboratories. That is, the measurement of results has the shortcomings of inconsistency and instability.

For biological specimens in liquid state, the absolute quantitative analysis of miRNA copy numbers can reveal the amount of miRNA in a given volume, which is a unit that is easier to understand and conform to nature, and is particularly suitable for liquid samples. The absolute quantitative analysis of copy numbers can facilitate a more accurate understanding on the relationship between miRNA and the disease, can reveal the degree of disease and prognosis more sophisticatedly. Bissel et al. use 10-fold diluted equimolar mixture of synthetic miRNA, and make use of microArray hybridization assay to make a calibration curve of miRNA copy number so as to achieve the absolute quantification of miRNA. The actual determination of amount of miR-122 in RNA of rat liver is about 53000 copies per 10 pg. Unfortunately, the minimum limit for this method is 1 amol, which is 6×106 copies, and this cannot meet the actual need of clinical diagnosis. In fact, because the principles of different microarray technological platforms are all realized by DNA/RNA hybridization, that the hybridization signal is not amplified with the presence of constraints of thermodynamic balance of hybridization, the method sensitivity is very difficult to break the lower limit of amol when the requirement of specificity of detection is maintained. Another factor that may cause discrepancies is that miRNA labeling reaction is limited by the terminal sequence and the secondary conformation of miRNA and the method used for labeling. It is difficult to mark all kinds of miRNAs in equal proportion, which causes discrimination bias for detection of different miRNAs.

Practical miRNA quantification methods must be sensitive, accurate and standardizable. The clinical samples are diversify and the have uncertain composition.

A simple example is that the components contained in the sera from different individuals may have no effect, inhibiting effect or promoting effect on the reverse transcription reaction and the PCR reaction. The current miR-seq, RT-qPCR, and microArray methods use RNA ligase, Reverse Transcriptase, and Taq polymerase, which are very sensitive to impurities in RNA samples. In addition, the technical design principles of these methods is try to get the quantity of the target for testing from the sample directly while no mechanism to balance the effect of impurities in the RNA samples is designed, therefore the results obtained is affected by the source of samples to become randomness, which increases the difficulty of standardization. Accordingly, strictly speaking, the absolute quantification is impossible to achieve by the existing quantitative methods.

For biological samples such as blood, the impurities contained in the purified RNA from sera of different individuals have an inhibitory or even promoting effect on the RT reaction and the PCR amplification efficiency, which increase the difficulty in the quantitative analysis using the conventional RT-qPCR methods. In addition, sample processing and purification usually involve the use of guanidine hydrochloride and other protein denaturant extraction method to obtain RNA of high purity. However, since the average size of miRNA is only 22 nt and high concentration of ethanol is required for long time precipitation to avoid loss, so the contradiction between purity and yield is more prominent. While purification method using resin column affinity can generally guarantee the purity of RNA, however the RNA integrity after purification has to be verified, that are the problems of miRNA loss and selectivity. Pathologic specimens obtained from patients are usually small and non-repeatable, and these problems have plagued the efforts to bring miRNA quantification to clinical applications.

SUMMARY OF THE PRESENT INVENTION

An object of the present invention is to: provide a new method for quantitative measurement of short-chain RNA to improve sensitivity, accuracy and standardization.

The technical solutions according to the preferred embodiment of the present invention are as follows: a method of quantitatively measurement of microRNAs using amplified fragment length polymorphism of DNA, comprising the following steps of:

first, utilizing at least two types of synthetic microRNA which has no natural homologous sequence when compared to a short-chain RNA for testing as an internal standard for measurement; and mixing the synthetic microRNA, which is used as the internal standard, with different molecule numbers to form a standard molecular gradient of dynamic microRNA;

then, mixing the short-chain RNA for testing with an equal amount of the dynamic microRNA standard; processing RNA reverse transcription, cDNA tailing, PCR synchronous amplification and fluorescence quantitative analysis of DNA length polymorphism fragment of PCR products to measure a relative ratio of fluorescence intensity of DNA fragment produced from the amplification of the short-chain RNA for testing based on the standard fluorescence intensity gradient of dynamic microRNA, thereby achieving a relative quantification of the short-chain RNA for testing.

According to the present invention, first, in the test sample, different number of molecules of synthetic microRNA as a dynamic microRNA standard is added to mix with the short-chain RNA for testing. Simultaneous detection is carried out in the same reaction. The standard quantity of molecule measured by simultaneous detection is defined as the standard scale of dynamic quantification. The relative peaks of the short-chain RNA for testing is obtained. In order to avoid mixing of sequence of short-chain RNA for testing in the test sample, the synthetic microRNA which is used as the internal standard is required to have no natural homologous sequence with the short-chain RNA for testing. Factor of Impurities or reaction effect have the same degree of impact on the short-chain RNA for testing in the test sample and the dynamic microRNA standard molecule. This design concept is clearly different from the existing methods. While the method of the present invention has sufficient sensitivity and accuracy, a certain degree of tolerance to impurities in the test sample is provided. This provides the advantageous effect of capability of comparing testing results of different samples between different operators and laboratories and so standardization can be implement easily. The effect of external factors such as RNA, especially short-chain RNA purification, sample quality, equipment, operations and supplies on measurement results of RNA, especially the measurement results of short-chain RNA can be counterbalanced.

According to a preferred embodiment of the present invention, after measuring a relative ratio of intensity of the short-chain RNA for testing to the standard gradient of dynamic microRNA, the sequence of the short-chain RNA for testing is used as a template to synthesis the reference short-chained RNA. The sequence of the reference short-chained RNA is the same as the sequence of the short-chain RNA for testing but has a different molecule number. Based on a relative ratio on the standard gradient of dynamic microRNA, a calibration curve of number of molecules versus relative intensity is obtained. Through the calibration curve, the ratio of relative intensity of the short-chain RNA for testing is used to calculate the absolute number of molecules of the short-chain RNA in the test sample.

Compare the relative measurement values of utilizing a known number of synthetic target RNA and same microRNA standard to obtain a calibration curve and the absolute number of RNA for testing is determined. Thus, the absolute quantitative result of the RNA for testing can be obtained.

According to a preferred embodiment of the present invention, the short-chain RNA for testing is miRNA or siRNA.

The method of the present invention can be used for measurement for different kind of living organism or determination of species (qualitative) and content (quantitative) of miRNA, siRNA and RNA in purified RNA. Small interfering RNA (siRNA) has the same physical and chemical properties as miRNA, and the above method can also be suitable for use in qualitative and quantitative measurement of siRNA. The present invention is also suitable for use in identification of one or some smaller sequence in RNA so as to achieve the qualitative and quantitative measurement of different kind of RNA, and is particularly suitable for short-chain RNA such as miRNA.

More and more studies have revealed that variation of miRNA and small RNA expression level is linked to the diagnosis and prognosis of disease. Pathological specimens obtained from a patient are usually small and non-repeatable while the purification method of miRNA and small RNA still cannot meet the needs of the current identification method. The present invention can utilize the offset effect to impurities in miRNA sample to carry out accurate quantification of miRNA for testing, to meet the needs of measurement to achieve clinical diagnosis, prognosis, criminal investigation and etc. through relative or absolute quantitative measurement of miRNA. miRNA signature is the expression level of several to tens of miRNA which is associated with a life phenomenon in a particular sample, and its change pattern may reveal related physiological or pathological changes. According to an application of the present invention, the miRNA signature can be identified easily, quickly, sensitively and accurately under one or several reactions, thus facilitating the application of miRNA signature in clinical diagnosis and research studies.

The present invention provides a method for performing absolute quantitative detection of the molecule number of RNA, especially miRNA, by the quantitative analysis of DNA fragment length polymorphism fluorescence (miRNA-derived Fragment Length Polymorphism Assay, which is referred to as "miRFLP quantitative analysis in the present invention). miRFLP quantitative analysis utilize three types of synthetic microRNA which has no natural homologous sequence as the internal standard, these three types of internal standard of miRNA is mixed with different molecule number to form a standard molecular gradient of dynamic microRNA, then an equal amount of the dynamic microRNA standard is mixed with the short-chain RNA for testing, through processing four steps of miRNA reverse transcription, cDNA tailing, PCR amplification, and fluorescence fragment length polymorphism analysis of PCR products, measure a relative ratio of fluorescence intensity of DNA fragment produced from the amplification of the short-chain RNA for testing based on the standard fluorescence intensity gradient of dynamic microRNA. Utilize the molecule number of synthetic reference short-chain RNA for testing and its relative fluorescence intensity to output a conversion curve of absolute quantity of short-chain RNA, thereby calculating the absolute content of short-chain RNA for testing.

According to a preferred embodiment of the present invention, in the process of RNA reverse transcription, the primer used is omega primer.

According to the present invention, the omega primer, in particularly, refers to the omega primer disclosed in the PCT application number PCT/CN2013/070525. The omega primer is used as the primer probes for the miRFLP quantitative assay reactions of the present invention. The omega primer contains an extremely stable secondary stem-loop structure, which can avoid the formation of primer dimer, enhance terminal priming accuracy and effectively separate probe region and coding region of the primer. By adding or subtracting the number of bases of the coding region, length encoding for different primers can be processed easily. Meanwhile, in the same reverse transcription reaction, different type of miRNA can be transformed to cDNA fragments of different lengths. Through simultaneous amplification of PCR, polymorphism analysis of fluorescence fragment length can be processed. Thus, the key technical issue for detecting multiple types of miRNA in a single reaction is solved.

Referring to FIG. 1, the miRFLP reaction includes four steps: miRNA reverse transcription, cDNA tailing, PCR amplification, and fluorescence fragment length polymorphism analysis of PCR products. The first step of the reaction is to hybridize miRNAs and omega primers. The miRNAs are paired with complementary probes. Then, reverse transcriptase is used to synthesis cDNA by using unpaired 3' terminal of miRNA as the template. After removing RNA, the newly synthesized cDNA and the 3' oligonucleotide primer containing a common PCR target undergo hybridization while DNA polymerase is used to fill the single-stranded gap after DNA pairing starting from 3' terminal of cDNA. After this combination, the correctly assembled cDNAs have the same 5' and 3' terminal sequences, which can process synchronous proportional amplification by a pair of fluorescent PCR primers. The amplified products is separated by capillary gel electrophoresis and the fluorescence intensity of PCR fragments of different lengths are determined and the miRFLP analysis spectrum is completed.

According to a preferred embodiment of the present invention, in the process of RNA reverse transcription, the primer used is stem-loop primer.

According to still further preferred embodiments, the stem-loop primer is length-encoded stem-loop primer.

According to still further preferred embodiments, the process of length-encoding is: adding different number of bases between a PCR target site of the stem-loop primer and a probe sequence, and adjusting a base sequence at the 5' terminal of the primer such that a secondary structure of the stem-loop primer remains unchanged.

Primer probe with stem-loop structure (Applied Biosystems, Inc, such as those disclosed by PCT/CN2013/070525) simultaneously and quantitatively converts multiple small RNA to cDNA. Likewise, through the above miRFLP reaction pathways, process cDNA products tailing. After reaction, process fluorescence fragment length polymorphism analysis through PCR synchronous amplification. The experimental results show that stem loop primers can also be used in the design of the present invention as long as a coding region for variable length is added. Also, the stem-loop primers and the omega primers can be used interchangeably or simultaneously when the number of miRNA target is a limited number.

According to a preferred embodiments, the calibration curve is logarithmically regressed and expressed as $aX^b$, where a and b are constants and are determined by actual values of measurement of the different number of synthetic microRNAs.

According to a preferred embodiments, the number of types of synthetic microRNA which has no natural homologous sequence when compared to a short-chain RNA for testing equals to three. Since the relationship between the fluorescence intensity and the amount of fluorescent material is not linear, at least three types is required to determine the regression of the quadratic equation. Using the three types of synthetic small RNAs can not only achieving the quantitative determination requirements, but also provide a relatively economical effect in the detection process.

In miRFLP quantitative analysis, the realization of intermediate products in each step and the signal amplification are both processed in linear or near linear quantification. Therefore, the fluorescence intensity of the amplified DNA fragment is linearly quantitatively related to the molecule number of the target miRNA. Because of the objective limitation of linear quantitative range of the DNA analyzer fluorescence probe, the response curve between the fluorescence intensity of the instrument probe and the amount of fluorescent material is suitable for the conversion between the fluorescence intensity measured and the molecule number of the target for testing. In order to determine the response curve of the instrument probe, we have selected a PCR products which has multiple fraction for testing. After serial dilution, the sample is used for fluorescence quantitative analysis by using ABI 3730xl model DNA Analyzer. The analysis confirmed that the correlation between the dilution factor and the measured fluorescence intensity in the range of 25-25000 FU fit the regression relationship of the quadratic equation, where the average R-square is greater than 0.9999. In this method, the standard dynamic miRNA and target fluorescence signal amplification of sample is carried out by synchronous and near linear quantification method. The regression of quadratic equation is applicable to the calculation of the relative fluorescence intensity of the miRNA to the standard dynamic miRNA. The modern DNA sequencer has a very high sensitivity and dynamic detection range (ABI 3730 DNA Analyzer: 5-31000 FU). Different manufacturers or different types of DNA fluorescence quantitative analyzer can be applied to the above method for calibration of applicable fluorescence response curve and range so as to select the most suitable, that is the most accurate, regression method.

Because of the influence of various external factors on the quantification method, the measured miRNA is not the absolute number of miRNAs, but the ratio of the miRNA for testing to the fluorescence intensity gradient of the standard dynamic miRNA. The ratio reflects the ratio of the miRNA molecules number to standard dynamic miRNA molecules number. Because the miRNA for testing and the standard dynamic miRNA are detected in the same reaction with synchronous amplification, the influence of external factors are eliminated. The number of molecules used in the standard dynamic miRNA is constant and the ratio of relative fluorescence intensity of miRNA for testing can objectively reflect the number of miRNAs for testing in different reactions.

Use serial dilutions of synthetic miRNA for testing with known molecule number as a reference and compare with standard dynamic miRNA can determine the calibration curve of the relative ratio of miRNA for testing and the molecule number of the miRNA for testing. The relative ratio of the miRNA for testing is converted to its miRNA absolute copy number. The use of two or three fold dilutions of the synthetic miRNA reference can also accurately determine the measurement range and the approximate error range of each concentration point. Thereby helping to improve the reliability and standardization of the resulting data analysis results. The regression model analysis for data obtained from 10 actual measurements with three-fold serial dilution by using IBM SPSS Statistics 20 statistical software. We found that the relationship between the relative fluorescence intensity of miRNAs and the molecule number fit the power regression of the logarithm equation, the R-square of the goodness of fit in the applicable detection range is greater than 0.99. Calibration of miRNA references is easy to standardize and can be used to correct operational errors between different laboratories, allowing data from different laboratories to be comparable.

Because different miRNA probes and 3' oligonucleotides have different Tm values, even under the same reaction conditions, their thermodynamic effects also lead to different miRNAs to have different calibration curves. Since there is no universal quantitative calibration curve for miRNAs, each miRNA must have its own standard curve of absolute quantification. The present invention is suitable for simultaneous identification of a plurality of miRNAs, and a plurality of synthetic miRNA reference substances can also be used in combination, which greatly reducing the number of required reactions. For example, to complete a calibration curve for nine different miRNAs, a three-fold dilution is used to prepare a standard curve for covering $50\text{-}5\times10^5$ molecule assay range, ten different concentrations of standard miRNA reference are required. If standard RT-qPCR assays were used, at least 90 reactions will be required to complete the production of the standard curve. With the method of synchronous detection of multiple target of the present invention, nine synthetic miRNAs can be mixed and used as templates, and the absolute calibration curve of nine kinds of miRNAs can be completed in only ten reactions.

Accordingly, based on the above technical solutions, the present invention has the following advantageous effect: compared to current methods, the miRFLP quantitative analysis of the present invention at least has the following advantageous effect:

1. Absolute Quantification: The absolute quantitation of miRNAs can be achieved by eliminating the interference of complex samples and RNA purity level with the dynamic small RNA standard molecules formed by the reaction of the sample RNA in the same reaction chamber.

2. High specificity: ability to identify miRNAs that differ by only one base or in the same family.

3. High sensitivity: the loading range of a single copy of cell miRNA assay is: 0.1 µg-1 ng total RNA;

4. Measurement range: Accurate quantitative measurement within the range of 100-106 copies number, relative quantitative measurement if beyond this range;

5. Objective results: internal control is established as an indicator of negative results for RT or PCR reaction failure, the accuracy of detection of gene fragment is ±0.2 base.

6. Good repeatability: controllable synthetic miRNA standard reference ensures reproducibility and comparability between different operators and different laboratories, thus facilitating method standardization.

7. Suitable for RNA crude extract: Accurate and objective measurement of miRNA expression levels directly from patient samples such as serum and plasma with good repeatability and reliable results.

BRIEF DESCRIPTION OF THE DRAWINGS

In FIG. 2, the y-axis FU refers to the fluorescence intensity and "☐" symbol marks the randomly selected DNA fragments.

In FIG. 3, "A" is a DNA fragment of 62.00 nt, "B" is a DNA fragment of 91.22 nt, the FU in the y-axis is the unit for fluorescence intensity.

In FIGS. 4A and 4B, "Std 1", "Std 2", "Std 3" represent the fluorescent DNA fragments of the dynamic miRNA standards (std 1, std 2, and std 3) respectively, "1", "2", "3", "4" represent reaction 1, reaction 2, reaction 3 and reaction 4 respectively, "a" represents the fluorescent DNA fragments of miR-92a, "b" represents the fluorescent DNA fragments of miR-92b, the y-axis is fluorescence intensity.

In the FIGS. 5A and 5B, "1" represents the quantitative result of blank control which only contains standard dynamic miRNA, "2-10" represent the target for testing with $2.5 \times 10^5$ to 244 number of added synthetic miR-92a molecules and equal amount of miR-92b. FIG. 5B is the graph of correspondence point of different miRNA copy number and its relative fluorescent intensity.

In FIG. 6, the x-axis is molecule number of miRNA, the y-axis is the relative fluorescent intensity.

In FIG. 7, from the top to the bottom, are the results for let-7b, let-7c, let-7d and let-7g, "Std 1", "Std 2", "Std 3" represent the same as the "Std 1", "Std 2", "Std 3" of FIG. 4A.

In FIG. 9, A: stem-loop primer designed for detection of Standard 1 RNA, where 4 bases (square) are placed between the 5' terminal of PCR target (arrow) and the probe as marker. Stem ring dG=−13.71. B: stem-loop primer designed for detection of Standard 2 RNA, where 7 bases (square) are placed between the 5' terminal of PCR target (arrow) and the probe as marker. Stem ring dG=−13.09.

DETAILED DESCRIPTION OF THE PREFERRED EMBODIMENT

Figure 1A:
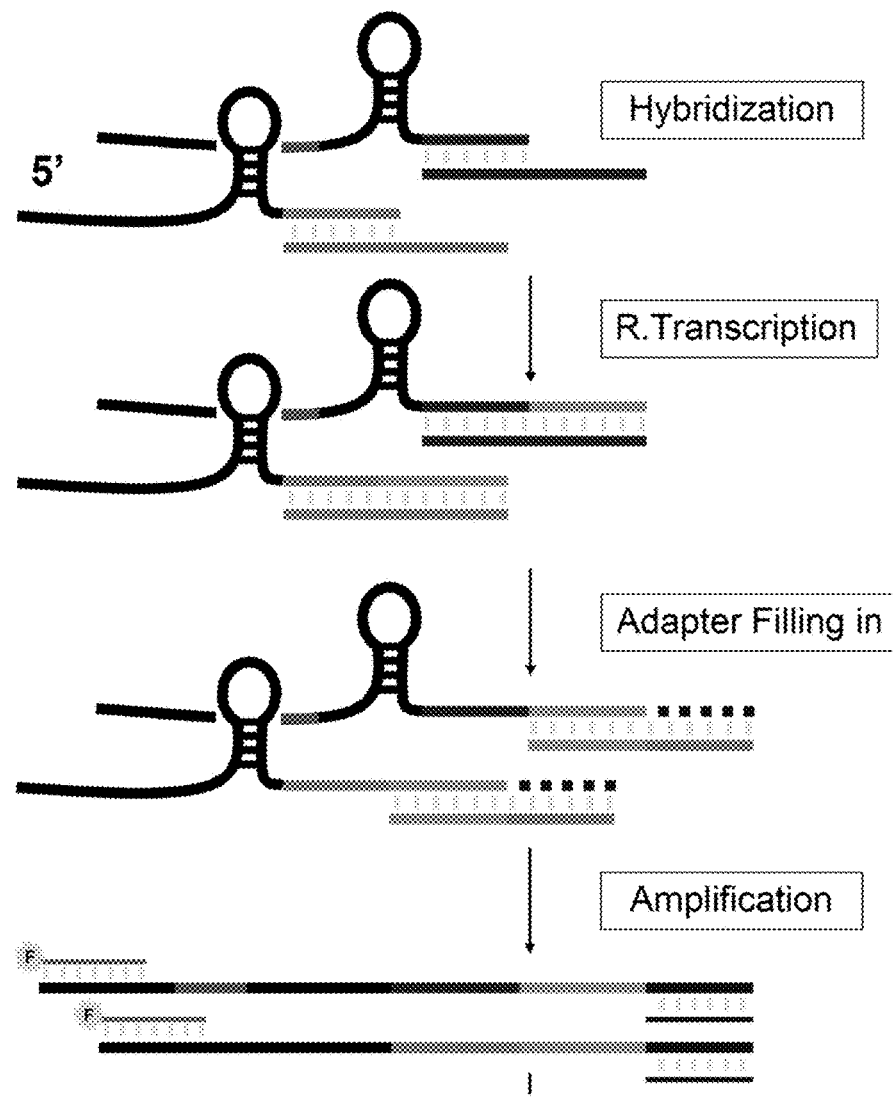
FIGS. 1A and 1B illustrate a reaction process and measurement principle of miRFLP quantitative analysis.

The present invention is further described in details with the accompanying figures and embodiments.

In order to further illustrate the object, technical feature and advantageous effect of the present invention, the present invention is further described in details with the accompanying figures and embodiments. One skilled in the art will understand that the embodiment of the present invention as shown in the drawings and described above is exemplary only and not intended to be limiting.

Figure 1B:
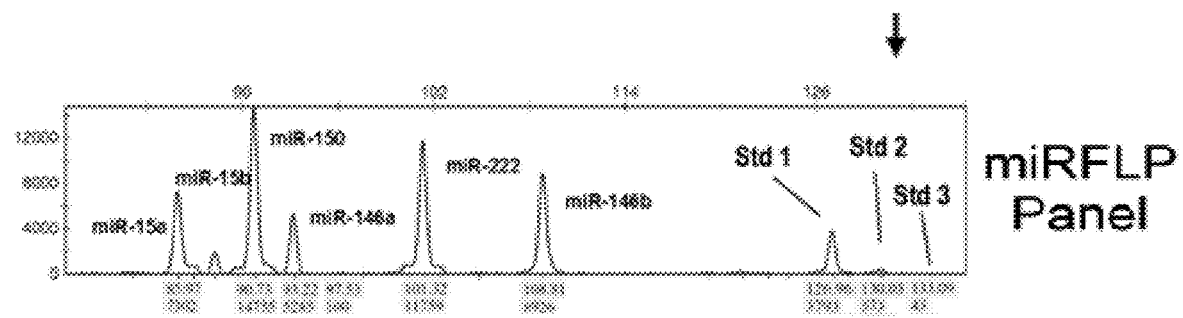

Embodiment 1 Reaction Process and Measurement Principle of miRFLP Quantitative Analysis In this embodiment, omega primer is used as an example to illustrate the reaction process and measurement principle of miRFLP Referring to FIGS. 1A and 1B of the drawings, miRFLP reaction consists of four steps: miRNA reverse transcription, cDNA tailing, PCR synchronous amplification, and fluorescence fragment length polymorphism analysis of PCR products. The first step of the reaction is to hybridize miRNAs and omega primers. The miRNAs are paired with complementary probes. Then, reverse transcriptase is used to synthesis cDNA by using unpaired 3' terminal of miRNA as the template. After removing RNA, the newly synthesized cDNA and the 3' oligonucleotide primer containing a common PCR target undergo hybridization while DNA polymerase is used to fill the single-stranded gap after DNA pairing starting from 3' terminal of cDNA. After this combination, the correctly assembled cDNAs have the same 5' and 3' terminal sequences, which can process synchronous proportional amplification by a pair of fluorescent PCR primers. The amplified products are separated by capillary gel electrophoresis and the fluorescence intensity of PCR fragments of different lengths are determined and the miRFLP analysis spectrum is completed. FIG. 1B refers to the last step in the entire miRFLP quantitative analysis.

Embodiment 2: Determination Test of Fluorescence Intensity of PCR Fluorescent Labeled Products with Equal Times Dilution The fluorescence intensity measured by fluorescence quantitative analyzer has a direct proportional relationship to the number of fluorescent substances to be measured. This relationship is related to the configuration of the fluorescent probe, that is, different fluorescent probes have different fluorescence response curve. For ABI's Prizma 310 DNA sequencer, the number of fluorescent substances to be measured is in a linear quantitative relationship when the measured fluorescence intensity is in the range of 5-7000 FU, and the relationship changes to a parabola when the fluorescence intensity is greater than 7000FU. Different fluorescent probes of different instruments have different response characteristics which can affect the regression relationship between the measured fluorescence intensity and amount of fluorescence to be measured.

Figure 2:
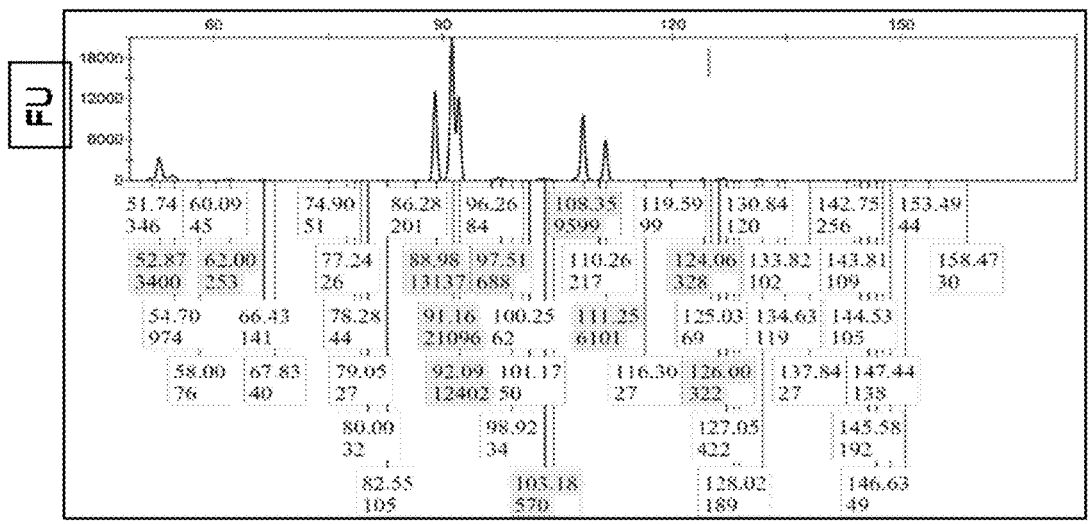
FIG. 2 is a fluorescence spectrum of DNA fragment length of randomly selected fluorescent PCR product which has a plurality of miscellaneous peaks and is diluted by 25 times.

According to this embodiment, calibration is carried out by 2-fold serial dilutions of the PCR products for Fluorescence Response Curve of ABI 3730xl model DNA Analyzer. In this experiment, the fluorescent PCR products which has more than one fraction and has a relative great fluorescence intensity variation is randomly selected. Dilute with 1×TE at 25, 50, 100, 200 and 400 times and then analyze by ABI 3730xl model DNA Analyzer. FIG. 2 is the fluorescence spectrum of a sample of the fluorescent PCR product which is diluted by 25 times. Eleven DNA fragments with peaks of 253-25000FU are selected and their fluorescence readings at different dilution level are statistically calculated (see Table 1)

Figure 3:
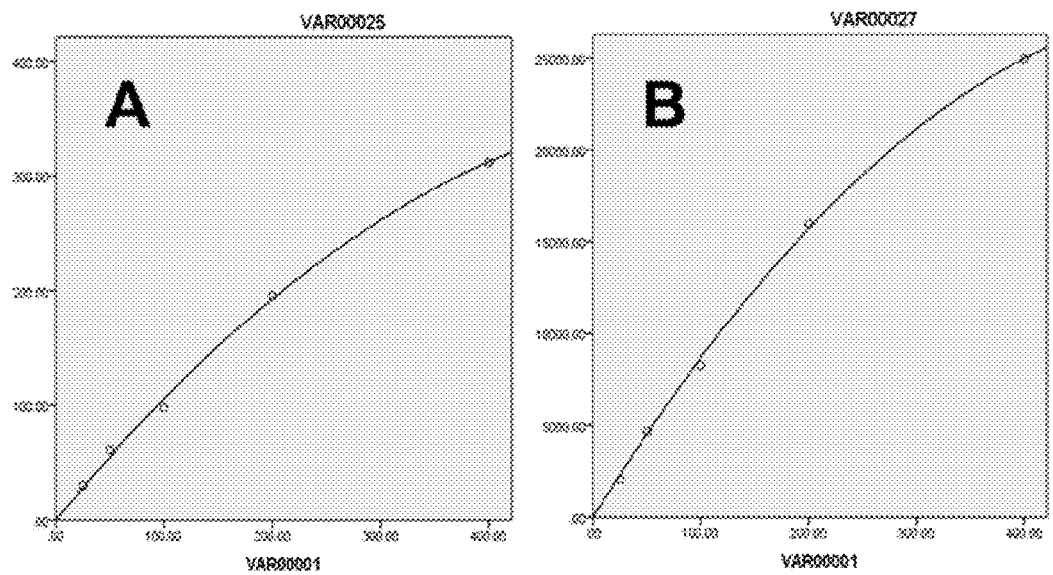
FIG. 3 illustrates a regression curve of DNA fragments which has a length of 62.00 nt and 91.22 nt(B) at different dilution levels, where the measured fluorescence value of the fragment and the dilution factor has a relation which fulfils the quadratic equation.

The optimal assessment of the regression curve is carried out for the correspondence relationship between the dilution factor and the measured fluorescence intensity values by IBM SPSS Statistics 20 statistical software. The results show that a quadratic regression curve is applicable to describe the relationship between the fluorescence intensity of all fragments and the dilution factor, where the R-squared of goodness of fit of the regression are greater than 0.999. Accordingly, the correspondence relationship between the fluorescence intensity of DNA fragments measured by ABI 3730xl model DNA Analyzer and amount of fluorescence substances can be calculated accurately by using the regression curve of quadratic equation in one unknown, rather than a simple linear quantitative relationship. Repeated experiments show that the absolute values of the same sample in different batches can be different, but this quadratic equation of the regression model is not affected. FIG. 3 illustrates a regression curve of fragments with low abundance (A: 30FU-312FU) and fragments with great abundance (B: 2052FU-24949FU) after serial dilution levels. Different manufacturers or DNA fluorescence quantitative analysis with different models can also use the above method to process calibration for applicable fluorescence response curve and range so as to select the most suitable regression, which is also the most accurate regression.

searches by the Sangers miRbase version 20 database showed no homologous sequences. Mix 4 µl of hybridization stock solution with 4l of the RNA sample for testing and add 2 µl of a 10 nM mixture of omega probes (containing probes for std1, 2, 3 and miR-92a and miR-92b, see Table 2 for probes sequences). After mixing evenly, carry out hybridization. The conditions for hybridization reaction are: 55 C for 10 minutes, and then from 55 C to 20 C at a rate of one degree per minute. Add 2 µl of reverse transcriptase mixture (1 µl of MMTV reverse transcriptase, 0.5 µl of dNTP, 0.5 µl of water, Takara), after mixing, keep at 25° C. for 30 minutes, 37 C for 10 minutes and denature at 85° C. for 5 minutes. Take 5 µl the RT product to add to 15 µl 3'adapter primer buffer (10 µl of JumpStart™ Taq ReadyMix, 2 µl of 100 nM 3' Oligonucleotide adapter primers, 1 µl of 0.1 µg/µl RNase A, 2 µl of Sterile water, Sigma), reaction conditions: 95 C for 2 minutes, 60c for 10 minutes, 5 cycles for 55c for 1 minute to 30c for 5 minutes, keep at 20c for 30 minutes, increase from 42 C to 68 C at a rate of 1 C per minute, keep at 72 C for 5 minutes.

Take 5 µl to add to 25 µl PCR reaction solution prepared by 15 µl JumpStart™ Taq ReadyMix (Sigma), 0.5 µM PCR

TABLE 1

The fluorescence values are measured at various dilution level by using the ABI 3730xl model DNA Analyzer for the PCR products used in FIG. 2 which is diluted by 25, 50, 100, 200, and 400 times and the R-square of the goodness of fit after regression with quadratic equation by using statistical analysis software IBM SPSS Statistics 20:

| | Dilution Factor | PCR fragment Length | | | | | | | | | |
|---|---|---|---|---|---|---|---|---|---|---|---|
| | | 52.87 nt | 62.00 nt | 88.98 nt | 91.16 nt | 92.09 nt | 97.51 nt | 103.18 nt | 108.35 nt | 111.25 nt | 124.06 nt | 126.00 nt |
| Repeat #1 | 25x | 3400 | 253 | 13137 | 21096 | 12402 | 688 | 570 | 9599 | 6101 | 328 | 322 |
| | 50x | 2180 | 172 | 8881 | 14113 | 8308 | 459 | 337 | 6253 | 3966 | 220 | 213 |
| | 100x | 1190 | 89 | 4852 | 7807 | 4683 | 250 | 191 | 3546 | 2175 | 123 | 130 |
| | 200x | 640 | 53 | 2594 | 4197 | 2512 | 140 | 104 | 1877 | 1125 | 59 | 67 |
| | 400x | 304 | 23 | 1211 | 1997 | 1180 | 70 | 50 | 918 | 552 | 36 | |
| | R square | 1.000 | 0.999 | 1.000 | 1.000 | 1.000 | 1.000 | 1.000 | 1.000 | 1.000 | 1.000 | 1.000 |
| Repeat #2 | 25x | 3501 | 265 | 13147 | 21005 | 11907 | 694 | 482 | 9494 | 5886 | 317 | 351 |
| | 50x | 2171 | 163 | 8195 | 13460 | 7643 | 444 | 325 | 6076 | 3647 | 207 | 210 |
| | 100x | 1235 | 93 | 4747 | 7570 | 4275 | 260 | 186 | 3328 | 2019 | 120 | 121 |
| | 200x | 582 | 46 | 2210 | 3569 | 2021 | 114 | 86 | 1552 | 905 | 48 | 60 |
| | 400x | 257 | 21 | 1544 | 1890 | 942 | 66 | 44 | 1060 | 571 | 34 | 40 |
| | R square | 1.000 | 1.000 | 1.000 | 1.000 | 1.000 | 0.999 | 1.000 | 1.000 | 1.000 | 0.999 | 1.000 |
| Repeat #3 | 25x | 4015 | 312 | 15315 | 24949 | 14592 | 813 | 725 | 11584 | 7171 | 382 | 394 |
| | 50x | 2540 | 196 | 10055 | 15981 | 9542 | 538 | 380 | 7187 | 4495 | 247 | 245 |
| | 100x | 1301 | 98 | 5191 | 8263 | 4872 | 285 | 203 | 3646 | 2274 | 117 | 136 |
| | 200x | 726 | 61 | 2945 | 4660 | 2820 | 166 | 114 | 2037 | 1256 | 74 | 78 |
| | 400x | 307 | 30 | 1259 | 2052 | 1176 | 70 | 53 | 888 | 563 | 34 | 52 |
| | R square | 1.000 | 0.999 | 1.000 | 1.000 | 1.000 | 1.000 | 1.000 | 1.000 | 1.000 | 0.999 | 1.000 |

Embodiment 3 Experiments of miRFLP Quantitative Analysis for miR-92a and miR-92

In miRFLP quantitative analysis, the miRNA for testing is mixed with standard dynamic microRNA, then processed through miRNA reverse transcription, cDNA tailing modification and synchronous fluorescent PCR amplification, and finally DNA fragment length and fluorescence quantitative analysis are performed by DNA sequencer. Specifically, first prepare stock solution:

2 µl of 5×RT buffer, 1 µl of 10 mM MgSO$_4$, and 1 µl of a standard dynamic miRNA mixture, the mixture includes "standard 1 RNA" (i.e., "std1" in FIG. 4A, the same applies hereinafter) having a molecule number of 3×10$^6$, "standard 2 RNA" (i.e., "std2" in FIG. 4A, the same applies hereinafter) having a molecule number of ×10$^5$, "standard 3 RNA" (i.e., "std3" in FIG. 4A, the same applies hereinafter) having a molecule number of 3×10$^4$, the RNA sequence of the standard dynamic miRNA is shown in Table 2. Sequence primers and 10 µl of water. Carry out fluorescence PCR amplification, reaction conditions: cycle of 95° C. for 2 minutes, 40 cycles for 10 seconds at 95° C., 68° C. for 3 minutes and 72° C. for 30 seconds. The universal PCR primers are: [5Fam] GTGCTGAGTCACGAGGTATTCTA and CACCGACAGGAGACCTGTTCT (purchased from GenScript). After the reaction is completed, the PCR products are diluted by 1:20 or 1:50 and then fluorescence fragment length polymorphism analysis is carried out by using ABI 3730xl type DNA analyzer. The results of miRFLP analysis spectrum are shown in FIGS. 4A and 4B.

Figure 4A:
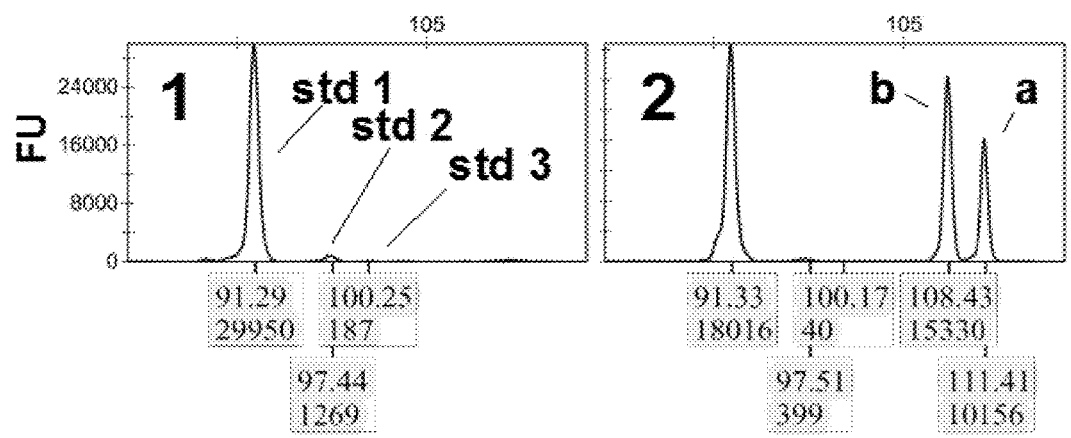
FIGS. 4A and 4B illustrate miRFLP analysis spectrum of standard dynamic miRNA and miRNA at various concentration.
Figure 4B:
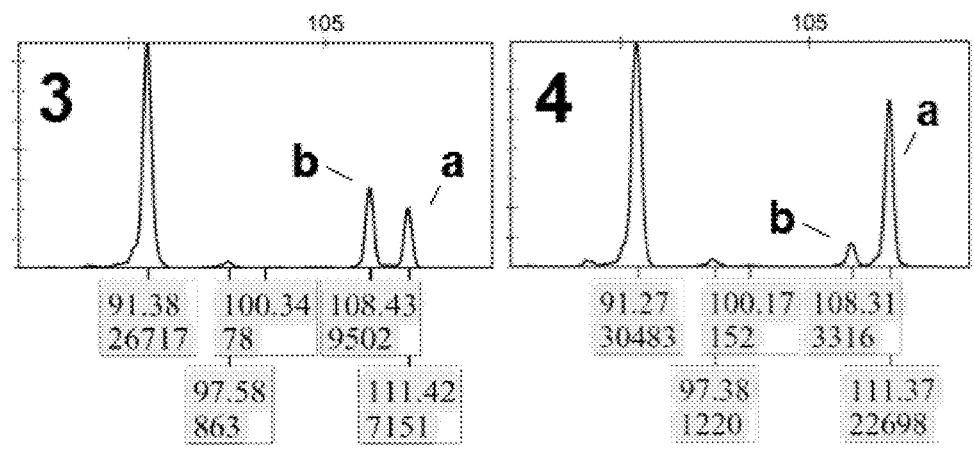

In FIG. 4A, reaction 1 is a blank control assay containing only the standard dynamic miRNA molecules; in reaction 2, 2.5×10$^5$ miR-92a molecules and an equal amount of miR-92b are added as the target for testing. In FIG. 4B, 3.1×10$^4$ miR-92a and an equal amount of miR-92b are added as the target for testing in reaction 3. In reaction 4, 78 pg of H1299 total RNA is added.

In the miRFLP analysis profiles of FIGS. 4A and 4B, DNA fragments of different lengths represent different miRNA molecules (the value above the peak refers to fragment length, nt), the fluorescence intensity reflects the relative amount of the miRNA (the value below the peak refers to fluorescence intensity, FU). Fluorescence intensities measured by different standards dynamic miRNA in the same reaction form a fluorescence intensity gradient corresponding to its molecule number. The absolute numbers of the various standard dynamic miRNA that are proportionately placed in different reactions are consistent. However, due to various reasons of different nature, such as the operation, equipment, supplies, reagents, measurement conditions, the absolute determination value of fluorescence intensity is affected and significant differences are shown. (such as the peaks of std 1 in reaction 1 and reaction 3) As the dilution factor of the target for testing is relatively smaller, the concentration of the preservation solution used for RNA preservation in Reaction 2 is higher than that in Reaction 3, which affected the efficiency of RT or PCR reaction, resulting in a change in the fluorescence intensity gradient of standard dynamic miRNA. Because the target for testing and the standard dynamic miRNA are mixed evenly before the reaction, this factor which affect the reaction efficiency is the same to the target for testing and the standard dynamic miRNA. The relative ratio of the fluorescence intensity of target for testing to the standard dynamic fluorescence intensity gradient can be used to objectively determine the ratio of molecules between the target for testing and the standard dynamic miRNA.

Through the design and optimization of the reaction conditions, the effect of the latter two factors can be minimized to a ignoreable level. which can reduce the influence of the latter two to a negligible extent. But the influence of probe Tm on the fluorescence intensity of the target cannot be ignored.

Therefore it is necessary to use the calibration curve between a known number of molecules of targets for testing and the relative fluorescence intensity in order to convert the relative fluorescence intensity of the target for testing to actual molecule number of the targets for testing. By using synthetic miRNAs with serial dilution as the target for testing, the conversion curves of the relative fluorescence intensity and the target molecules number can be obtained the target molecule to be measured.

Figure 5A:
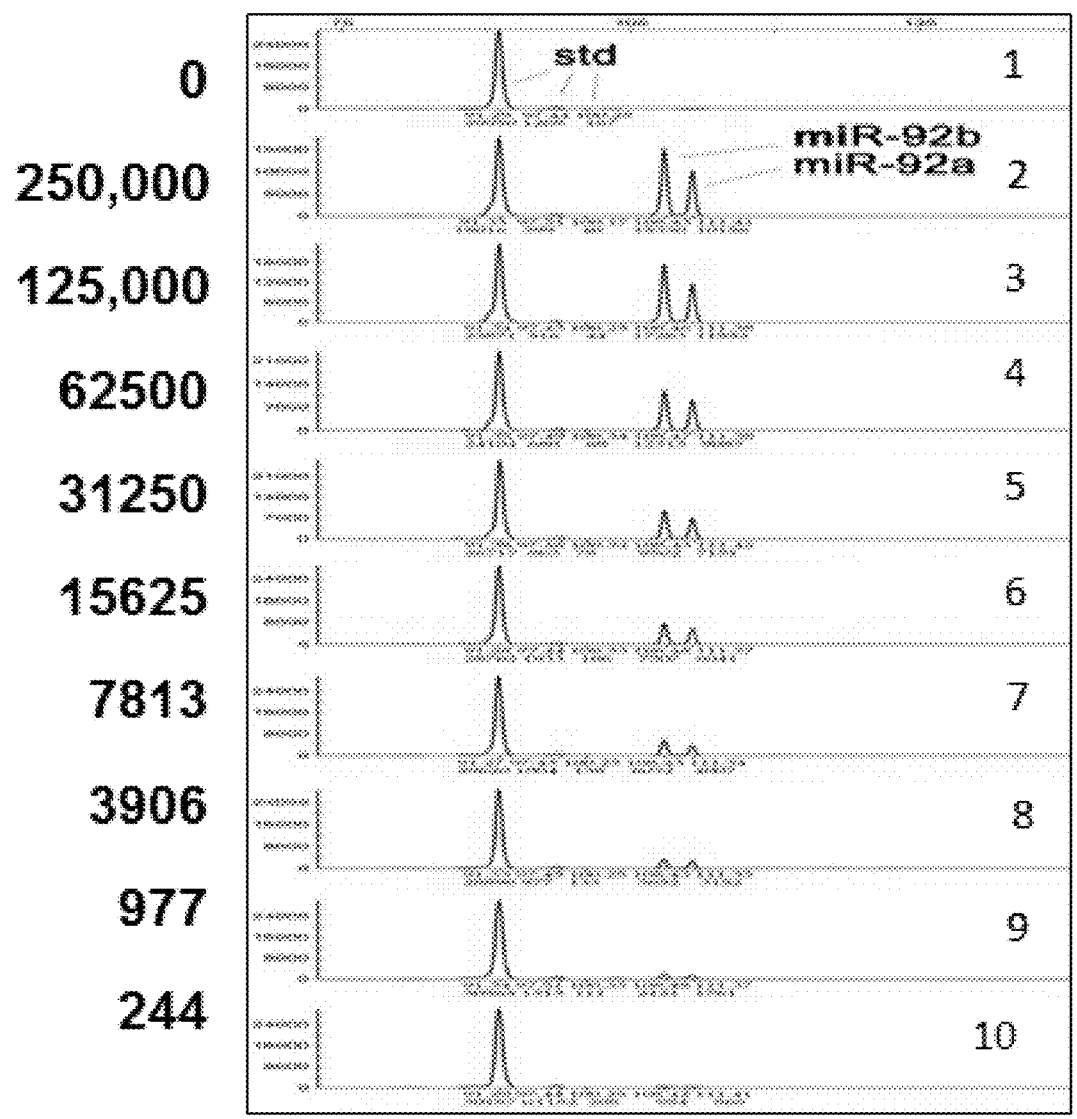
FIGS. 5A and 5B are miRFLP assay spectrum and standard curve for different molecule numbers of miR-92a and miR-92b.

In this embodiment, an equal number of synthetic miR-92a and miR-92b nucleic acid small molecules of 2-fold dilution level is used as the target for testing. The relative fluorescence intensity of the synthetic miR-92a and miR-92b at nine different dilutions are determined according to the conditions of the miRFLP analysis of miR-92 in Embodiment 3. This experiment group is set up for assay reaction of 3.12 ng, 0.312 ng, 0.0312 ng of A549 cell RNA, 0.222 ng of Hela cell RNA, and 0.25 ng of H1299 cell RNA. Three replicates are set up for each assay to determine the error range for the assay. The numerals on the left in FIG. 5A show the number of molecules of miR-92a and miR-92b in each reaction. The right side is the miRFLP analysis spec-

TABLE 2 miRFLP Quantitive Analysis for omega primer of miR-92a and miR-92 (The base sequences are SEQ ID NO. 1, SEQ ID NO. 2 respectively; the base seequences of the omega-omega primer used are both SEQ ID NO. 3; the base sequences of the 3' oligonucleotide adapter primers (that is the 3' Adapter in Table 2) are SEQ ID NO. 4, SEQ ID NO. 5 respectively), the standard dynamic miRNA (Std 1, 2, 3)(their base sequences are SEQ ID NO. 6, SEQ ID NO. 7, SEQ ID NO. 8 respectively; the base sequences of the omega-omega primer used are SEQ ID NO. 9, SEQ ID NO. 10, SEQ ID NO. 11 respectively, the base sequences of the 3' oligonucleotide adapter primers are both SEQ ID NO. 12) and its composition: in the table, the average molecular weight (308.95 daltons) of dG, dC, dA and dT is 1 nt, the molecular weight of 5' fluorophore is 474.5.

| RNA Name | Omega Primer 5'-3' | miRNA sequence 5'-3' | RNA Copy per Rx | 3' Adapter 5'-3' | Fragmen Length Expected | Actual |
|---|---|---|---|---|---|---|
| Std 1 | GTGCTGAGTCACGAGGTATTCTA T GGCACGCTTTCATTAGCGTGCC TCGGATTATGA | ACCGUACAUCU UCAUAAUCCGA | $4 \times 10^5$ | CACCGACAGGAGACCT GTTCT ACCGTACATCT | 91.01 nt | 91.35 nt |
| Std 2 | GTGCTGAGTCACGAGGTATTCTA TGTTCTT GGCACGCTTTCATTAGCGTGCC TCGGATATGCA | ACCGUACAUCU UGCAUAUCCGA | $4 \times 10^4$ | | 96.90 nt | 97.49 nt |
| Std 3 | GTGCTGAGTCACGAGGTATTCTA TGAACTTGAC GGCACGCTTTCATTAGCGTGCC TTGGATTACTA | ACCGUACAUCU UAGUAAUCCGA | $4 \times 10^3$ | | 99.89 nt | 100.34 nt |
| miR-92b-3p | GTGCTGAGTCACGAGGTATTCTA TGTTCTTGAG TTATATTCA GGCACGCTTTCATTAGCGTGCC G | UAUUGCACUCG UCCCGGCCUCC | varies | CACCGACAGGAGACCTGT TCTATAC TATTGCACTCG | 113.19 nt | 108.47 nt |
| miR-92a-3p | GAGGCCGGGA | UAUUGCACUUG UCCCGGCCUGU | varies | CACCGACAGGAGACCTGTT CTATACATCTATTGCACTTG | 116.20 nt | 111.38 nt |

Figure 5B:
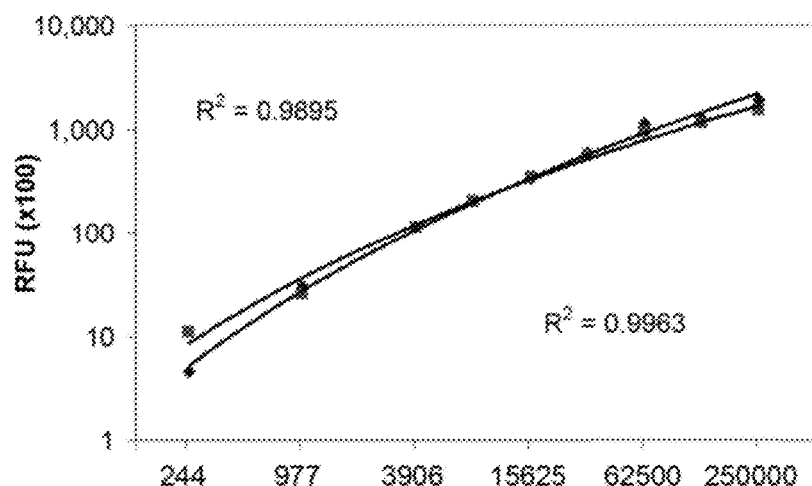

Embodiment 4 Test of Calibration Curve of miRFLP Quantitative Analysis and Quantitative Analysis of miR-92a and miR-92 in Total RNA MiRFLP quantitative analysis reaction for the reverse transcription, modification and amplification reactions of the small RNAs in the same reaction is in a linear equal ratio manner. Dynamic standard fluorescence intensity gradient can exclude the influence of external factors on the measurement. However, the differences in the Tm, PCR fragment length and conformation of the probe still affected the fluorescence intensity of the DNA fragment.

trum, which shows that the fluorescence intensity of miR-92a and miR-92b decreased gradually with the decrease of the molecule number for testing. Use Microsoft Excel table for statistical analysis of regression for fluorescence intensity of standard dynamic miRNA and their corresponding molecule numbers to obtain the best quadrative equation, and in this equation, substituting the fluorescence intensity of the target for testing to obtain the relative fluorescence intensity of the target for testing to the standard dynamic small RNA. FIG. 5B is a point correspondence graph of different miRNA copy numbers and their relative fluorescence intensities, and the trend is consistent with the law of power regression. The regression curves of miR-92b and miR-92a are: $0.0001x^{7.4237}$ and $0.0013x^{6.4765}$ respectively, the R-square of goodness of fit are greater than 0.98.

Table 3 lists the fluorescence intensity results of the three cellular RNAs and the relative fluorescence intensity (RFU) values converted from the measured fluorescence intensity of miR-92b and miR-92a using the fluorescence intensity of the standard dynamic small RNA in each reaction. Using the power of regression of the calibration curve of the miR-92a and miR-92b, the amount of miRNA in cell RNA and their respective error ranges are obtained. The results of three 10-fold dilutions of RNA from A549 cells show that in a RNA loading range of 0.03 ng to 3 ng, The error of detection of miR-92b and miR-92a are 10.13% and 12.63% respectively. It is shown that miRFLP assays have little effect on sample quantitation and has great reliability.

and its measured relative fluorescent intensity relative to the graph and relative to the logarithmic regression. The calibration regression curves of the molecule number of miR-92b, miR-92a and miR-25 are $4.3965x^{3.4854}$, $9.9139x^{3.0082}$ and $4.4131x^{3.3164}$ respectively, the R-square of goodness of fit are greater than 0.98. Table 4 lists the error ranges (C.V) for the relative fluorescence intensities at various molecule number obtained from three replicate experiments. This show that the effective quantitative detection range of miR-25 miRFLP analysis is 38-250,000. The detection error range at the level of 38 molecules is 104%. Outside this detection range, a relative quantitative measurement of the target for testing can be determined. One important reason of miRNA as an ideal biomarker is that the range of changes of miRNA molecule number resulted from

TABLE 3

The miR-92a and miR-92b levels in total RNA of cell are determined by miRFLP method. The total RNA concentration of cell is determined by Qubic 2.0 Fluorescence Quantifier.

| | Fluorescence Unit | | | | | RFU | | miR copy/ng RNA | | | |
|---|---|---|---|---|---|---|---|---|---|---|---|
| RNA amount | Std #1 | Std #2 | Std #3 | miR-92b | miR-92a | miR-2b | miR-92a | miR-92b | C.V | miR-92a | C.V |
| 3.12 ng A549 RNA | 27418 | 682 | 112 | 960 | 13251 | 5635 | 151696 | 7,110 | 12.61% | 394,996 | 6.35% |
| | 31659 | 690 | 128 | 1246 | 15984 | 6934 | 166186 | | | | |
| | 32118 | 662 | 133 | 1103 | 15867 | 5929 | 164125 | | | | |
| 0.312 ng A549 RNA | 32073 | 689 | 168 | 370 | 4029 | 1273 | 27763 | 8,681 | 35.34% | 345,449 | 25.50% |
| | 27276 | 405 | 143 | 159 | 2313 | 668 | 19071 | | | | |
| | 30185 | 496 | 119 | 212 | 3316 | 963 | 27564 | | | | |
| 0.0312 ng A549 RNA | 31859 | 928 | 206 | 68 | 1149 | 93 | 4306 | 8,248 | 24.83% | 307,042 | 86.27% |
| | 31378 | 1880 | 241 | 146 | 372 | 145 | 553 | | | | |
| | 31741 | 1087 | 186 | 87 | 1507 | 131 | 6093 | | | | |
| 0.222 ng Hela RNA | 31356 | 1297 | 264 | 1487 | 7360 | 4567 | 46128 | 54,097 | 27.03% | 747,141 | 40.34% |
| | 7536 | 198 | 39 | 184 | 946 | 3058 | 25880 | | | | |
| | 31718 | 804 | 162 | 776 | 4509 | 3144 | 30931 | | | | |
| 0.250 ng H1299 RNA | 31569 | 892 | 141 | 300 | 3488 | 963 | 22175 | 7,195 | 56.09% | 509,963 | 24.15% |
| | 31825 | 1209 | 272 | 221 | 5702 | 295 | 32215 | | | | |
| | 31733 | 1004 | 199 | 322 | 4895 | 752 | 30252 | | | | |

Figure 6:
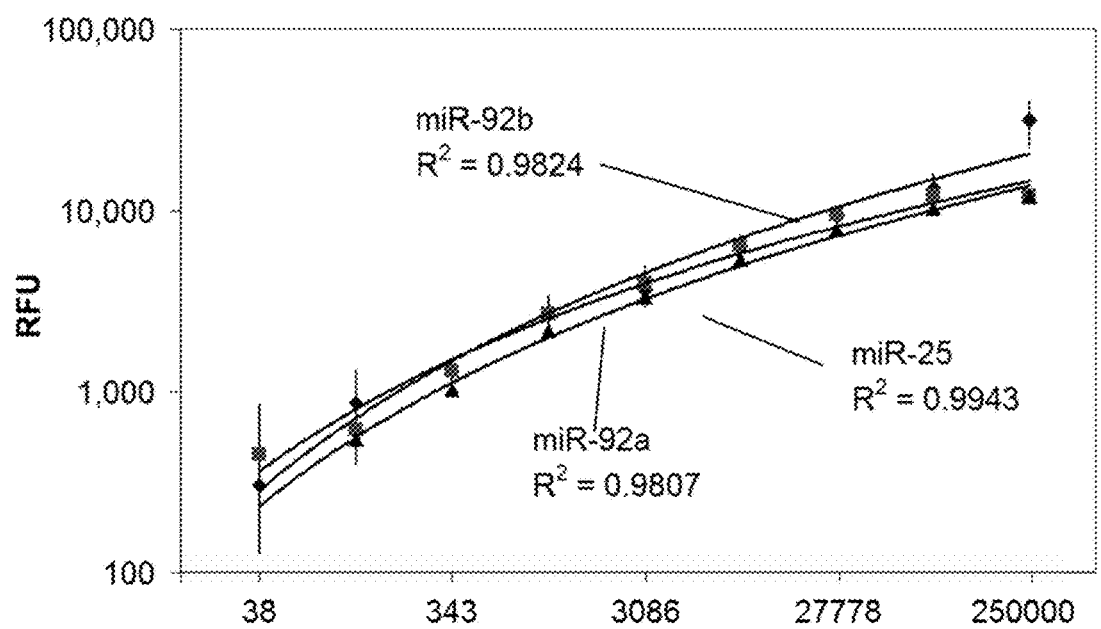
FIG. 6 illustrates the results of detection range and repeatability of correction curve of miR-25 family members measured by miRFLP method.

Embodiment 5 Test of Quantitative Measurement Range and Error Verification of miRFLP Quantitative Analysis Mixture of small molecules of synthetic miR-2, miR-92a and miR-92b nucleic acid of equal amount and three-fold dilution is used as a target for testing. Based on the miRFLP assay conditions of miR-92 in embodiment 3, the primer and standard dynamic small RNA as listed in Table 5 is used for measuring the relative fluorescent intensity of the synthetic miR-25, miR-92a and miR-92b under nine different dilution level. The molecules number of synthetic miRNA in each reaction are: 250,000, 83,333, 27,778, 9,259, 3,086, 1,029, 343, 114 respectively. There are 38 number of mixture of equal volume of miRNAs, miR-92a and miR-92b synthetic miRNAs, as well as blank control. Three replicates are set up for each assay to determine the error range for the assay. Statistical regression is carried out for the fluorescence intensity of the standard dynamic small RNA in each reaction and the corresponding molecule numbers by using the Microsoft Excel table to obtain the best quadratic equation. In this equation, the fluorescence intensity of the target for testing is substituted and then the relative fluorescence intensity of the target for testing relative to the standard dynamic small RNA is obtained. FIG. 6 shows the goodness-of-fit of the scatter of the various miRNA molecule numbers the physiological and pathological effect is very great, and so the diagnostic sensitivity is very high. The range of quantitative measurement of miRNA, the detection error level and the objectivity determined by the MiRFLP analysis are all beyond the current identification methods to meet the clinical requirements of miRNA analysis, that the MiRFLP analysis has a very good application prospect.

TABLE 4

Determination of error range of mi-R25 family at various level of molecule number by miRFLP Quantitative Analysis

| Ref miRNA Copies | miR-92b C.V | miR-92a C.V | miR-25 C.V |
|---|---|---|---|
| 250,000 | 29.19% | 3.40% | 4.84% |
| 83,333 | 21.10% | 8.39% | 8.46% |
| 27,778 | 14.96% | 4.00% | 6.66% |
| 9,259 | 16.19% | 5.49% | 2.93% |
| 3,086 | 13.13% | 25.08% | 17.95% |
| 1,029 | 17.04% | 26.68% | 24.54% |
| 343 | 13.38% | 17.85% | 23.72% |
| 114 | 54.04% | 26.95% | 33.07% |
| 38 | 103.62% | 88.01% | |

TABLE 5

Table of base sequences and composition of omega primer, standard dynamic miRNA (Std 1, 2, 3) and 3' oligonucleotide adapter primers (3' Adapter) of miR25 family at various level of molecule number determined by miRFLP Quantitative Analysis

| RNA | Omega Primer 5'-3' | miRNA sequence 5'-3' | RNA copy per Rx | 3' Adapter 5'-3' | Fragmen Length Expected | Actual |
|---|---|---|---|---|---|---|
| Std 1 | GTGCTGAGTCACGAGGTATTCTA T GGCACGCTTTCATTAGCGTGCC TCGGATTATGA | ACCGUACAUCU UCAUAAUCCGA | 4 X 10^5 | CACCGACAGGAGACCT GTTCT ACCGTACATCT | 91.01 nt | 91.35 nt |
| Std 2 | GTGCTGAGTCACGAGGTATTCTA TGTTCTT GGCACGCTTTCATTAGCGTGCC TCGGATATGCA | ACCGUACAUCU UGCAUAUCCGA | 4 X 10^4 | | 96.90 nt | 97.49 nt |
| Std 3 | GTGCTGAGTCACGAGGTATTCTA TGAACTTGAC GGCACGCTTTCATTAGCGTGCC TCGGATTACTA | ACCGUACAUCU UAGUAAUCCGA | 4 X 10^3 | | 99.89 nt | 100.34 nt |
| miR-92b-3p | GTGCTGAGTCACGAGGTATTCTA TGTTCTTGAG TTATATTCA GGCACGCTTTCATTAGCGTGCC G GAGGCCGGGA | UAUUGCACUCG UCCCGGCCUCC | varies | CACCGACAGGAGACCTGT TCTATAC TATTGCACTCG | 113.19 nt | 108.47 nt |
| miR-92a-3p | | UAUUGCACUUG UCCCGGCCUGU | varies | CACCGACAGGAGACCTGTT CTATACATCTATTGCACTTG | 116.20 nt | 111.38 nt |

*Average Molecular Weight (308.95 delton) of dG, dC, dA and dT is counted as 1 nt, MW of 5' Fam: 474.5

Figure 7:
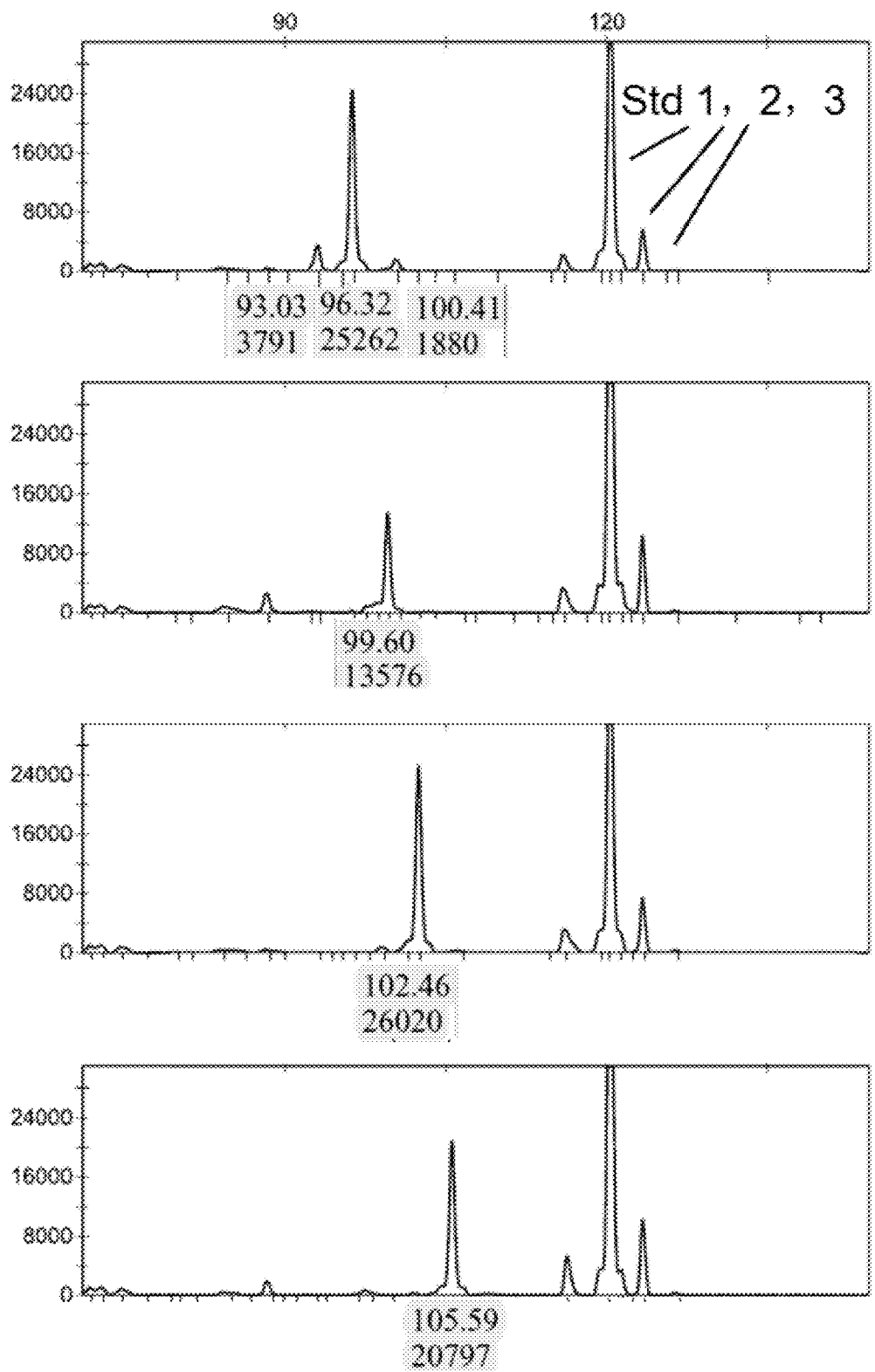
FIG. 7 is a graphical representation of miRFLP quantitative analysis profiles of the Let-7 family for individual Let-7 member.

Embodiment 6 Specificity Verification Test for the Method of miRFLP Quantitative Analysis Determine the relative fluorescence intensities of let-7b, let-7c, let-7d and let-7g respectively by using parts of the let-7 miRFLP profile as determined by using the primers and standard dynamic miRNA listed in Table 6 under the same conditions of the miRFLP Analysis requirements in the embodiment 3. The number of synthetic miRNA molecules added as a template in each reaction is 12,500.

Wherein the sequence of let-7b is:
(SEQ ID NO. 13)
ugagguaguag guuguguggu u the sequence of let-7c is
(SEQ ID NO. 14)
ugagguaguag guuguauggu u the sequence of let-7d is
(SEQ ID NO. 15)
agagguaguag guugcauagu u the sequence of let-7g is
(SEQ ID NO. 16)
ugagguaguag uuuguacaguu The resulting miRFLP spectrum is shown in FIG. 7. As seen from FIG. 7, the miRFLP assay has a very high specificity and is capable of distinguishing miRNA molecules which differ from each other by one single base. When 12500 number of different members of Let-7 as templates is used and miRFLP spectrum of Let-7 family is used for separate testing of individual let-7 members, the results show that the largest cross-reaction of let-7 members occurs between Let-7b and Let-7f and its value is less that 5%, which is similar to the specificity of the stem-loop primer of ABI company. However, the difference is that the cross-reactivity assay of the present invention is carried out with omega mixed probe which can detect all of the Let-7 members. That is its realization is achieved in reaction for multi-target measurement, rather than in a single primer. This assessment of specificity is closer to the practical application.

TABLE 6

The standard dynamic miRNA (Std 1, 2, 3) and composition of omega primer (the base sequences are SEQ ID NO. 17, SEQ ID NO. 18, SEQ ID NO. 19, SEQ ID NO. 20 respectively, the base sequence of the 3' oligonucleotide adapter primers (3' Adapter) used are all SEQ ID NO: 21) of some of the let-7 family members (let-7b, let-7c, let-7d, let-7g) by miRFLP quantitative analysis.

| RNA | Omega Primer 5'-3' | miRNA Sequence 5'-3' | RNA copy per Rx | 5'-3' | Fragment Length Expected | Actual |
|---|---|---|---|---|---|---|
| Std 1 | GTGCTGAGTCACGAGGTATTCTA TGAATACcTTCAACTTGCAGTTACTGCAAG TCaT GGCACGCTTctTAGCGTGCC TCGGATATGCA | ACCGUACAUCU UCAUAAUCCGA | 4 X 10^5 | CACCGACAG GAGACCTGTT CT | 121.75 nt | 120.39 nt |
| Std 2 | GTGCTGAGTCACGAGGTATTCTA TGAATACcTTCAACTTGCAGTTACTGCAAG TCaT GGCACGCTTctTAGCGTGCCTTA TCGGATATGCA | ACCGUACAUCU UGCAUAUCCGA | 4 X 10^4 | ACCGTACATC T | 124.73 nt | 123.45 nt |
| Std 3 | GTGCTGAGTCACGAGGTATTCTA TGAATACcTTCAACTTGCAGTTACTGCAAG TCaT GGCACGCTTctTAGCGTGCCTTACTT TCGGATTACTA | ACCGUACAUCU UAGUAAUCCGA | 4 X 10^3 | | 127.56 nt | 126.49 nt |
| Let-7b | GTGCTGAGTCACGAGGTATTCTA AcTTcTAA GGCACGCTTctTAGCGTGCC AACCACACAAC | ugagguaguag guuguguggu u | 12500 | CACCGACAG GAGACCTGTT | 97.11 nt | 96.32 nt |
| Let-7c | GTGCTGAGTCACGAGGTATTCTA AcTTcTAAcaa GGCACGCTTctTAGCGTGCC AACCATACAAC | ugagguaguag guuguauggu u | 12500 | CT ACA TGAGGTAGTA | 100.08 nt | 99.60 nt |

TABLE 6-continued

The standard dynamic miRNA (Std 1, 2, 3) and composition of omega
primer (the base sequences are SEQ ID NO. 17, SEQ ID NO. 18, SEQ ID NO. 19, SEQ ID
NO. 20 respectively, the base sequence of the 3' oligonucleotide adapter primers (3'
Adapter) used are all SEQ ID NO: 21) of some of the let-7 family members (let-7b, let-
7c, let-7d, let-7g) by miRFLP quantitative analysis.

| RNA | Omega Primer 5'-3' | miRNA Sequence 5'-3' | RNA copy per Rx | 5'-3' | Fragment Length Expected | Actual |
|---|---|---|---|---|---|---|
| Let-7d | GTGCTGAGTCACGAGGTATTCTA AcTTcTAAcaaTCA GGCACGCTTctTAGCGTGCC AACTATGCAAC | agagguaguag guugcauaguu | 12500 | G DTT | 103.16 nt | 102.46 nt |
| Let-7g | GTGCTGAGTCACGAGGTATTCTAAcTTcTAAcaaTCAA CttCA GGCACGCTTctTAGCGTGCC AACTGTACAAA | ugagguaguag uuuguacaguu | 12500 | | 109.11 nt | 108.59 nt |

*Average Molecular Weight (308.95 delton) of dG, dC, dA and dT is counted as 1 nt, MW of 5' Fam: 474.5

Embodiment 7 Quantitative Analysis of miRFLP Using Stem-Loop Primers

Determine the relative fluorescence intensities of the synthetic miR-25 and miR-92b respectively by using the stem-loop primers and standard dynamic miRNA listed in Table 7 under the same conditions of the miRFLP Analysis requirements of miR-92 in the embodiment 3.

Figure 8:
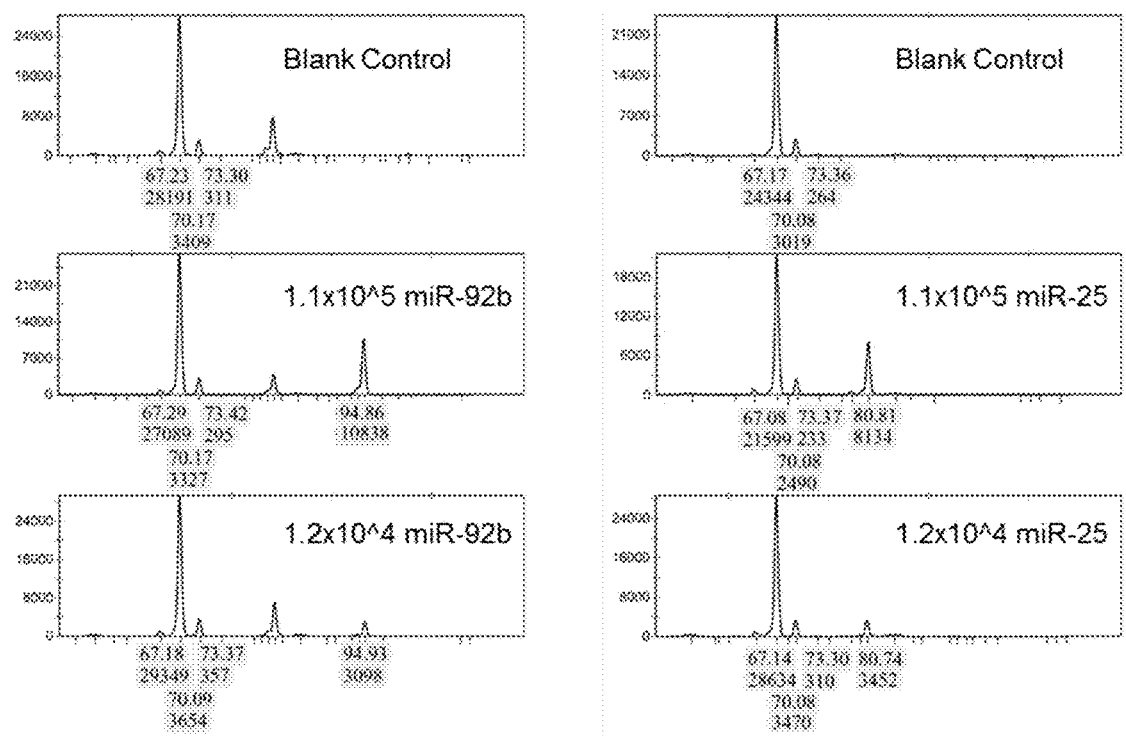
FIG. 8 shows the results of miRFLP analysis of miR-92b and miR-25 using stem-loop primer.

The analytical profile correctly shows the DNA fragments representing the target miRNA while the fluorescence intensity of the fragment is directly proportional to the usage amount of target miRNA. This suggests that stem-loop primers can also be used in the miRFLP analysis of miRNAs after certain level of optimization. The miRFLP analysis spectrum in FIG. 8 shows the results of quantitative results of miR-92b and miR-25 by using stem-loop primers. In FIG. 8, the correct DNA fragment representing miR-92b is 94.93 nt. The illustrations on the right shows miRFLP analysis of miR-25. The correct DNA fragment representing miR-25 is 80.74 nt. The relationship between fluorescence intensity and number of various miRNA templates as determined by miRFLP analysis by using stem-loop primers is similar to the results of miRFLP analysis by using omega primer, thus stem-loop primers can also be substituted for the omega primer to determine the absolute quantitation of miRNA by the same method.

Figure 9:
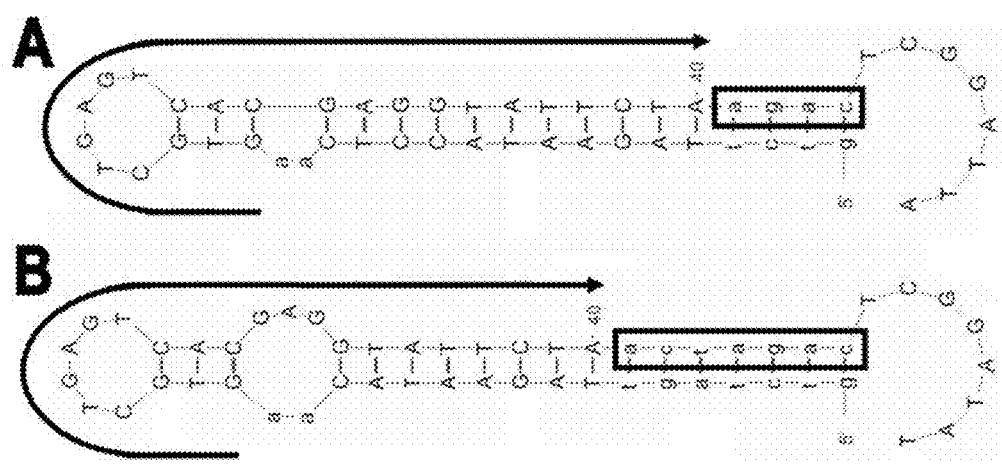
FIG. 9 shows stem-loop primers using the number of bases for encoding.

The original design of stem-loop primers is used to initiate reverse transcription of miRNAs. The original aim is to determine the concentration of target miRNAs using the qPCR amplification cycle while the PCR products with complementary sequences are quantitatively determined using fluorescently labeled hybridization probes. Therefore, the method of identifying the target RNA by using the polymorphism of PCR fragment length is not considered. Stem-loop primers can be used for reverse transcription of miRNAs as well as primers for synthetic cDNA in miRFLP analysis. Different numbers of bases are introduced as coding between the PCR target site of conventional stem-loop primer and the probe, and different miRNA targets can be distinguished in the same reaction, which meets the need for simultaneous detection of multiple miRNAs. FIG. 9 illustrates an exemplary design which utilizes the stem-loop primer probe with base number encoding and length polymorphism targeting miR-25 and miR-92b. In FIG. 9, the PCR fragment length of primer A is 67.17 nt and the PCR fragment length of primer B is 70.08 nt, which can be distinguished from the miRFLP analysis spectrum.

TABLE 7

Base sequences and composition of miR-25 and miR-92b omega
primer, standard dynamic miRNA (Std 1, 2, 3) and 3' oligonucleoti adapter primers (3'
Adapter) determined by miRFLP Quantitative Analysis

| | Size-coded stem loop primer 5'-3' | miRNA sequence 5'-3' | RNA copy per Rx | 3' Adapter 5'-3' | Fragment Length Expected | Actual |
|---|---|---|---|---|---|---|
| Std 1 | gtct TAGAATACCTC aa GTGCTGAGTC ACGAGGTATTCTA agac TCGGATTA | ACCGUACAUCU CAUAAUCCGA | $4 \times 10^5$ | CACCGACAGGAGACCT GTTCT GTACATCTTCA | 69.04 nt | 67.17 nt |
| Std 2 | gtctagtTAGAATACaaGTGCTGAGTCA CGAGGTATTCTA act agac TCGGATAT | ACCGUACAUCU UGCAUAUCCGA | $4 \times 10^4$ | CACCGACAGGAGACCT GTTCT GTACATCTTGC | 71.93 nt | 70.08 nt |
| Std 3 | gtct TAGAATACCTC aa GTGCTGAG TCACGAGGTATTCTA agac TCGGATTA | ACCGUACAUCU UAGUAAUCCGA | $4 \times 10^3$ | CACCGACAGGAGACCTGTT CT ATACGA GTACATCTTAG | 74.88 nt | 73.36 nt |
| miR-25-3p | gtct TAGAATACCTC aaa GTGCTGAGTC ACGAGGTATTCTA agac GGAGGCC | CAUUGCACUUG UCUCGGUCUGA | varies | CACCGACAGGAGACCTGTTCT TGTTCTTA TTCTCGTCATTCCACGACG TATTGCACTCG | 99.66 nt | 94.86 nt |
| miR-92b-3p | gtct TAGAATACCTC aaa GTGCTGA GTCACGAGGTATTCTA agac TCAGACC | UAUUGCACUCG UCCCGGCCUCC | varies | CACCGACAGGAGACCTG TTCT ATACAACACA CATTGCACTTG | 82.37 nt | 80.81 nt |

*Average Molecular Weight (308.95 delton) of dG, dC, dA and dT is counted as 1 nt, MW of 5' Fam: 474.5

What is claimed is:

1. A method of quantitatively measurement of short-chain RNAs using amplified fragment length polymorphism of DNA, characterized in that: said method comprises the following steps of:

first, utilizing at least two types of synthetic microRNA which has no natural homologous sequence when compared to a short-chain RNA for testing as an internal standard for measurement; and mixing the synthetic microRNA, which is used as the internal standard, with different molecule numbers to form a standard molecular gradient of dynamic microRNA;

then, mixing the short-chain RNA for testing with an equal amount of the dynamic microRNA standard; processing RNA reverse transcription, cDNA tailing, PCR synchronous amplification and fluorescence quantitative analysis of DNA length polymorphism fragment of PCR products to measure a relative ratio of fluorescence intensity of DNA fragment produced from the amplification of the short-chain RNA for testing based on the standard fluorescence intensity gradient of dynamic microRNA, thereby achieving a relative quantification of the short-chain RNA for testing.

2. The method of quantitatively measurement of microRNAs using amplified fragment length polymorphism of DNA according to claim 1, characterized in that: said method comprises the following steps of:

after measuring a relative ratio of fluorescence intensity of DNA fragment produced from the amplification of the short-chain RNA for testing relative to the standard fluorescence intensity gradient of dynamic microRNA, utilizing the short-chain RNA for testing as a template to synthesis short-chained RNA reference; then determining a relative ratio of RNA reference for testing at different molecular numbers on the standard fluorescence intensity gradient of dynamic microRNA, thereby obtaining a calibration curve of number of molecules relative intensity of the RNA reference for testing and calculating an absolute number of molecules of the short-chain RNA for testing in the test sample by utilizing the ratio of relative intensity of the short-chain RNA through the calibration curve.

3. The method of quantitatively measurement of short-chain RNA using amplified fragment length polymorphism of DNA according to claim 1, characterized in that: the short-chain RNA for testing refers to microRNA (miRNA) or small interfering RNA (siRNA).

4. The method of quantitatively measurement of short-chain RNA using amplified fragment length polymorphism of DNA according to claim 1, characterized in that: in the RNA reverse transcription, the primer used is omega primer.

5. The method of quantitatively measurement of short-chain RNA using amplified fragment length polymorphism of DNA according to claim 1, characterized in that: in the RNA reverse transcription, the primer used is stem-loop primer.

6. The method of quantitatively measurement of short-chain RNA using amplified fragment length polymorphism of DNA according to claim 5, characterized in that: the stem-loop primer refers to length-encoded stem-loop primer.

7. The method of quantitatively measurement of short-chain RNA using amplified fragment length polymorphism of DNA according to claim 6, characterized in that: the length-encoded stem-loop primer is produced by a length-encoding method comprising the steps of: adding different number of bases between a PCR target site of the stem-loop primer and a probe sequence, and adjusting a base sequence at the 5' terminal of the primer such that a secondary structure of the stem-loop remains unchanged.

8. The method of quantitatively measurement of short-chain RNA using amplified fragment length polymorphism of DNA according to claim 2, characterized in that: the calibration curve is logarithmically regressed and expressed as $aX^b$, where a and b are constants and are determined by actual values of measurement of the different number of synthetic microRNAs.

9. The method of quantitatively measurement of short-chain RNA using amplified fragment length polymorphism of DNA according to claim 1, characterized in that: a number of types of synthetic microRNA which has no natural homologous sequence when compared to a short-chain RNA for testing equals to three.

10. The method of quantitatively measurement of short-chain RNA using amplified fragment length polymorphism of DNA according to claim 2, characterized in that: the short-chain RNA for testing refers to microRNA (miRNA) or small interfering RNA (siRNA).

11. The method of quantitatively measurement of short-chain RNA using amplified fragment length polymorphism of DNA according to claim 2, characterized in that: in the RNA reverse transcription, the primer used is omega primer.

12. The method of quantitatively measurement of short-chain RNA using amplified fragment length polymorphism of DNA according to claim 2, characterized in that: in the RNA reverse transcription, the primer used is stem-loop primer.

13. The method of quantitatively measurement of short-chain RNA using amplified fragment length polymorphism of DNA according to claim 12, characterized in that: the stem-loop primer refers to length-encoded stem-loop primer.

14. The method of quantitatively measurement of short-chain RNA using amplified fragment length polymorphism of DNA according to claim 13, characterized in that: the length-encoded stem-loop primer is produced by a length-encoding method comprising the steps of: adding different number of bases between a PCR target site of the stem-loop primer and a probe sequence, and adjusting a base sequence at the 5' terminal of the primer such that a secondary structure of the stem-loop remains unchanged.

15. A fluorescent capillary electrophoresis method of quantitatively measurement of short-chain RNAs using amplified fragment length polymorphism of DNA, characterized in that: said method comprises the following steps of:

first, utilizing at least two types of synthetic microRNA which has no natural homologous sequence when compared to a short-chain RNA for testing as an internal standard for measurement; and mixing the synthetic microRNA, which is used as the internal standard, with different molecule numbers to form a standard molecular gradient of dynamic microRNA;

then, mixing the short-chain RNA for testing with an equal amount of the dynamic microRNA standard; processing RNA reverse transcription, cDNA tailing, PCR synchronous amplification and fluorescence quantitative analysis of DNA length polymorphism fragment of PCR products to measure a relative ratio of fluorescence intensity of DNA fragment produced from the amplification of the short-chain RNA for testing based on the standard fluorescence intensity gradient of dynamic microRNA, thereby achieving a relative quantification of the short-chain RNA for testing, utilizing the short-chain RNA for testing as a template to synthesis short-chained RNA reference; then determining a relative ratio of RNA reference for testing at different molecular numbers on the standard fluorescence intensity gradient of dynamic microRNA, thereby obtaining a calibration curve of number of molecules relative intensity of the RNA reference for testing and calculating an absolute number of molecules of the short-chain RNA for testing in the test sample by utilizing the ratio of relative intensity of the short-chain RNA through the calibration curve, wherein the short-chain RNA for testing refers to microRNA (miRNA).

* * * * *

UNITED STATES PATENT AND TRADEMARK OFFICE
CERTIFICATE OF CORRECTION

PATENT NO. : 10,266,880 B2  
APPLICATION NO. : 15/500027  
DATED : April 23, 2019  
INVENTOR(S) : Kai Xu et al.

Page 1 of 1

It is certified that error appears in the above-identified patent and that said Letters Patent is hereby corrected as shown below:

On the Title Page

The assignee information is added as follows:  
Assignee: Chengdu Nuoen Genomics Co., Ltd.,  
      Chengdu (CN)

Signed and Sealed this  
Twenty-eighth Day of April, 2020

Andrei Iancu  
*Director of the United States Patent and Trademark Office*

SEQUENCE LISTING

<160> NUMBER OF SEQ ID NOS: 21

<210> SEQ ID NO 1
<211> LENGTH: 22
<212> TYPE: RNA
<213> ORGANISM: Artificial Sequence
<220> FEATURE:
<223> OTHER INFORMATION: Synthesized

<400> SEQUENCE: 1
uauugcacuu gucccggccu gu                                              22

<210> SEQ ID NO 2
<211> LENGTH: 22
<212> TYPE: RNA
<213> ORGANISM: Artificial Sequence
<220> FEATURE:
<223> OTHER INFORMATION: Synthesized

<400> SEQUENCE: 2
uauugcacuc gucccggccu cc                                              22

<210> SEQ ID NO 3
<211> LENGTH: 75
<212> TYPE: DNA
<213> ORGANISM: Artificial Sequence
<220> FEATURE:
<223> OTHER INFORMATION: Synthesized

<400> SEQUENCE: 3
gtgctgagtc acgaggtatt ctatgttctt gagttatatt caggcacgct ttcattagcg    60
tgccggaggc cggga                                                     75

<210> SEQ ID NO 4
<211> LENGTH: 39
<212> TYPE: DNA
<213> ORGANISM: Artificial Sequence
<220> FEATURE:
<223> OTHER INFORMATION: Synthesized

<400> SEQUENCE: 4
caccgacagg agacctgttc tatacatcta ttgcacttg                            39

<210> SEQ ID NO 5
<211> LENGTH: 36
<212> TYPE: DNA
<213> ORGANISM: Artificial Sequence
<220> FEATURE:
<223> OTHER INFORMATION: Synthesized

<400> SEQUENCE: 5
caccgacagg agacctgttc tatactattg cactcg                               36

<210> SEQ ID NO 6
<211> LENGTH: 22
<212> TYPE: RNA
<213> ORGANISM: Artificial Sequence
<220> FEATURE:
<223> OTHER INFORMATION: Synthesized

<400> SEQUENCE: 6
accguacauc uucauaaucc ga                                              22

<210> SEQ ID NO 7
<211> LENGTH: 22

-continued

```
<212> TYPE: RNA
<213> ORGANISM: Artificial Sequence
<220> FEATURE:
<223> OTHER INFORMATION: Synthesized

<400> SEQUENCE: 7
accguacauc uugcauaucc ga                                          22

<210> SEQ ID NO 8
<211> LENGTH: 22
<212> TYPE: RNA
<213> ORGANISM: Artificial Sequence
<220> FEATURE:
<223> OTHER INFORMATION: Synthesized

<400> SEQUENCE: 8
accguacauc uuaguaaucc ga                                          22

<210> SEQ ID NO 9
<211> LENGTH: 57
<212> TYPE: DNA
<213> ORGANISM: Artificial Sequence
<220> FEATURE:
<223> OTHER INFORMATION: Synthesized

<400> SEQUENCE: 9
gtgctgagtc acgaggtatt ctatggcacg ctttcattag cgtgcctcgg attatga    57

<210> SEQ ID NO 10
<211> LENGTH: 63
<212> TYPE: DNA
<213> ORGANISM: Artificial Sequence
<220> FEATURE:
<223> OTHER INFORMATION: Synthesized

<400> SEQUENCE: 10
gtgctgagtc acgaggtatt ctatgttctt ggcacgcttt cattagcgtg cctcggatat 60
gca                                                               63

<210> SEQ ID NO 11
<211> LENGTH: 66
<212> TYPE: DNA
<213> ORGANISM: Artificial Sequence
<220> FEATURE:
<223> OTHER INFORMATION: Synthesized

<400> SEQUENCE: 11
gtgctgagtc acgaggtatt ctatgaactt gacggcacgc tttcattagc gtgcctcgga 60
ttacta                                                            66

<210> SEQ ID NO 12
<211> LENGTH: 32
<212> TYPE: DNA
<213> ORGANISM: Artificial Sequence
<220> FEATURE:
<223> OTHER INFORMATION: Synthesized

<400> SEQUENCE: 12
caccgacagg agacctgttc taccgtacat ct                               32

<210> SEQ ID NO 13
<211> LENGTH: 22
<212> TYPE: RNA
<213> ORGANISM: Artificial Sequence
<220> FEATURE:
```

```
<223> OTHER INFORMATION: Synthesized

<400> SEQUENCE: 13
ugagguagua gguugugugg uu                                              22

<210> SEQ ID NO 14
<211> LENGTH: 22
<212> TYPE: RNA
<213> ORGANISM: Artificial Sequence
<220> FEATURE:
<223> OTHER INFORMATION: Synthesized

<400> SEQUENCE: 14
ugagguagua gguuguaugg uu                                              22

<210> SEQ ID NO 15
<211> LENGTH: 22
<212> TYPE: RNA
<213> ORGANISM: Artificial Sequence
<220> FEATURE:
<223> OTHER INFORMATION: Synthesized

<400> SEQUENCE: 15
agagguagua gguugcauag uu                                              22

<210> SEQ ID NO 16
<211> LENGTH: 22
<212> TYPE: RNA
<213> ORGANISM: Artificial Sequence
<220> FEATURE:
<223> OTHER INFORMATION: Synthesized

<400> SEQUENCE: 16
ugagguagua guuguacag uu                                               22

<210> SEQ ID NO 17
<211> LENGTH: 62
<212> TYPE: DNA
<213> ORGANISM: Artificial Sequence
<220> FEATURE:
<223> OTHER INFORMATION: Synthesized

<400> SEQUENCE: 17
gtgctgagtc acgaggtatt ctaacttcta aggcacgctt cttagcgtgc caaccacaca    60
ac                                                                   62

<210> SEQ ID NO 18
<211> LENGTH: 65
<212> TYPE: DNA
<213> ORGANISM: Artificial Sequence
<220> FEATURE:
<223> OTHER INFORMATION: Synthesized

<400> SEQUENCE: 18
gtgctgagtc acgaggtatt ctaacttcta acaaggcacg cttcttagcg tgccaaccat    60
acaac                                                                65

<210> SEQ ID NO 19
<211> LENGTH: 68
<212> TYPE: DNA
<213> ORGANISM: Artificial Sequence
<220> FEATURE:
<223> OTHER INFORMATION: Synthesized

<400> SEQUENCE: 19
```

```
gtgctgagtc acgaggtatt ctaacttcta acaatcaggc acgcttctta gcgtgccaac      60
tatgcaac                                                               68

<210> SEQ ID NO 20
<211> LENGTH: 74
<212> TYPE: DNA
<213> ORGANISM: Artificial Sequence
<220> FEATURE:
<223> OTHER INFORMATION: Synthesized

<400> SEQUENCE: 20
gtgctgagtc acgaggtatt ctaacttcta acaatcaact tcaggcacgc ttcttagcgt      60
gccaactgta caaa                                                        74

<210> SEQ ID NO 21
<211> LENGTH: 38
<212> TYPE: DNA
<213> ORGANISM: Artificial Sequence
<220> FEATURE:
<223> OTHER INFORMATION: Synthesized

<400> SEQUENCE: 21
caccgacagg agacctgttc tacatgaggt agtagdtt                              38
```